US00PP23131P2

(12) United States Plant Patent
Kanazawa

(10) Patent No.: US PP23,131 P2
(45) Date of Patent: Oct. 23, 2012

(54) ***ANEMONE* PLANT NAMED 'PRETTY LADY JULIA'**

(50) Latin Name: *Anemone hupehensis*
Varietal Denomination: Pretty Lady Julia

(75) Inventor: Yoshiro Kanazawa, Fukushima-ken (JP)

(73) Assignee: Specialis Plants BV, Oude Wetering (NL)

( * ) Notice: Subject to any disclaimer, the term of this patent is extended or adjusted under 35 U.S.C. 154(b) by 0 days.

(21) Appl. No.: 13/135,324

(22) Filed: Jun. 30, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — C. A. Whealy

(57) ABSTRACT

A new and distinct cultivar of *Anemone* plant named 'Pretty Lady Julia', characterized by its upright and compact plant habit; vigorous growth habit; freely flowering habit; relatively large semi-double type flowers that are pink and light pink in color; and good garden performance.

2 Drawing Sheets

Botanical designation: *Anemone hupehensis.*
Cultivar denomination: 'PRETTY LADY JULIA'.

BACKGROUND OF THE INVENTION

The present invention relates to a new and distinct cultivar of *Anemone*, botanically known as *Anemone hupehensis* and hereinafter referred to by the name 'Pretty Lady Julia'.

The new *Anemone* plant is a product of a planned breeding program conducted by the Inventor in Higashisirakawa-gun, Fukushima-ken, Japan. The objective of the breeding program is to create new uniform and freely-flowering *Anemone* plants with large flowers and attractive flower color.

The new *Anemone* plant originated from a cross-pollination made by the Inventor in August, 2005 in Higashisirakawa-gun, Fukushima-ken, Japan of two unnamed proprietary selections of *Anemone hupehensis*, not patented. The new *Anemone* plant was discovered and selected by the Inventor as a single flowering plant within the progeny of the stated cross-pollination in a controlled greenhouse environment in Higashisirakawa-gun, Fukushima-ken, Japan in August, 2006.

Asexual reproduction of the new *Anemone* by root cuttings in a controlled environment in Higashisirakawa-gun, Fukushima-ken, Japan since October, 2006 has shown that the unique features of this new *Anemone* are stable and reproduced true to type in successive generations.

SUMMARY OF THE INVENTION

Plants of the new *Anemone* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'Pretty Lady Julia'. These characteristics in combination distinguish 'Pretty Lady Julia' as a new and distinct *Anemone* plant:

1. Upright and compact plant habit.
2. Vigorous growth habit.
3. Freely flowering habit.

4. Relatively large semi-double type flowers that are pink and light pink in color.
5. Good garden performance.

Plants of the new *Anemone* can be compared to plants of the female parent selection. Plants of the new *Anemone* differ primarily from plants of the female parent selection in the following characteristics:

1. Plants of the new *Anemone* are taller than plants of the female parent selection.
2. Plants of the new *Anemone* have semi-double type flowers whereas plants of the female parent selection have single type flowers.
3. Plants of the new *Anemone* and the female parent selection differ in flower color as plants of the female parent selection have dark pink-colored flowers.

Plants of the new *Anemone* can be compared to plants of the male parent selection. Plants of the new *Anemone* differ primarily from plants of the male parent selection in the following characteristics:

1. Plants of the new *Anemone* are shorter than plants of the male parent selection.
2. Plants of the new *Anemone* have semi-double type flowers whereas plants of the male parent selection have double type flowers.
3. Plants of the new *Anemone* and the male parent selection differ in flower color as plants of the male parent selection have dark pink-colored flowers.

Plants of the new *Anemone* can be compared to plants of *Anemone hupehensis* 'Splendens', not patented. In side-by-side comparisons conducted in Hillegom, The Netherlands, plants of the new *Anemone* and 'Splendens' differed primarily in the following characteristics:

1. Plants of the new *Anemone* were more compact than plants of 'Splendens'.
2. Plants of the new *Anemone* had semi-double type flowers whereas plants of 'Splendens' had single type flowers.
3. Plants of the new *Anemone* and 'Splendens' differed in flower color as plants of 'Splendens' had darker pink-colored flowers.

Plants of the new *Anemone* can also be compared to plants of *Anemone hupehensis* 'Prinz Heinrich', not patented. In side-by-side comparisons conducted in Hillegom, The Netherlands, plants of the new *Anemone* and 'Prinz Heinrich' differed primarily in the following characteristics:

1. Plants of the new *Anemone* were more compact than plants of 'Prinz Heinrich'.
2. Plants of the new *Anemone* and 'Prinz Heinrich' differed in flower color as plants of 'Prinz Heinrich' had dark pink-colored flowers.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'Pretty Lady Julia' in a container.

The photograph on the second sheet comprises a close-up view of a typical flower of 'Pretty Lady Julia'.

DETAILED BOTANICAL DESCRIPTION

The aforementioned photographs and following observations, measurements and values describe plants grown in 5-liter containers during the summer in an outdoor nursery in Vogelenzang, The Netherlands and under commercial practices. During the production of the plants, day temperatures ranged from 12° C. to 28° C. and night temperatures ranged from 4° C. to 14° C. Plants were one year old when the photographs and description were taken. In the following description, color references are made to The Royal Horticultural Society Colour Chart, 2007 Edition, except where general terms of ordinary dictionary significance are used.

Botanical classification: *Anemone hupehensis* 'Pretty Lady Julia'.

Parentage:

*Female, or seed, parent*.—Unnamed proprietary selection of *Anemone hupehensis*, not patented.

*Male, or pollen, parent*.—Unnamed proprietary selection of *Anemone hupehensis*, not patented.

Propagation:

*Time to initiate roots, summer*.—About one week at temperatures of 20° C.

*Time to initiate roots, winter*.—About two weeks at temperatures of 20° C.

*Time to produce a rooted young plant, summer*.—About six to nine weeks at temperatures of 15° C. to 17° C.

*Time to produce a rooted young plant, winter*.—About nine to ten weeks at temperatures of 15° C. to 17° C.

*Root description*.—Fine, fibrous; light brown in color.

*Rooting habit*.—Freely branching; medium density.

Plant description:

*Plant and growth habit*.—Perennial; upright plant habit with leaves developing from basal rosettes; about nine basal rosettes develop per plant; moderately vigorous to vigorous growth habit.

*Plant height*.—About 77 cm.

*Plant diameter*.—About 43 cm.

Foliage description:

*Arrangement*.—Alternate, compound with three leaflets per leaf.

*Length, leaves*.—About 9.8 cm.

*Width, leaves*.—About 7.6 cm.

*Length, leaflets*.—About 6 cm.

*Width, leaflets*.—About 4 cm.

*Shape, leaves*.—Broadly ovate.

*Shape, leaflets*.—Ovate to broadly ovate.

*Apex, leaflets*.—Acute.

*Base, leaflets*.—Obtuse to hastate.

*Margin, leaflets*.—Serrate.

*Texture, leaflets, upper and lower surfaces*.—Pubescent.

*Venation pattern, leaflets*.—Palmate, laciniate.

*Color*.—Developing leaflets, upper surface: Close to 143A to 143B. Developing leaflets, lower surface: Close to 138B to 138C. Fully expanded leaflets, upper surface: Close to N137A to N137B; venation, close to 144A. Fully expanded leaflets, lower surface: Close to 148B; venation, close to 144B.

*Leaf petiole*.—Length: About 13.7 cm. Diameter: About 2.5 mm. Texture, upper and lower surfaces: Pubescent. Color, upper and lower surfaces: Close to 144A.

Flower description:

*Flower arrangement and flowering habit*.—Semi-double type rose-like flowers arranged in simple and compound cymes with long peduncles; freely flowering habit with eight flowers develop per inflorescence; flowers face mostly upright to slightly outwardly.

*Fragrance*.—None detected.

*Natural flowering season*.—Plants of the new *Anemone* flower during the late summer in The Netherlands.

*Flower longevity*.—Individual flowers last about one week on the plant; flowers not persistent.

*Inflorescence height*.—About 23.8 cm.

*Inflorescence diameter*.—About 17.4 cm.

*Flower diameter*.—About 5.9 cm.

*Flower length (depth)*.—About 2.5 cm.

*Flower buds*.—Length: About 8 mm. Diameter: About 1 cm. Shape: Flattened globular. Color: Close to 202C to 202D.

*Petals*.—Absent.

*Sepals*.—Quantity and arrangement: About 28 arranged in a several whorls, radially symmetrical. Length: About 2.9 cm. Width: About 1.2 cm. Shape: Elliptic to narrowly elliptic. Apex: Obtuse. Base: Acute. Margin: Entire. Texture, upper surface: Glabrous, smooth, velvety. Texture, lower surface: Pubescent. Color: When opening, upper and lower surfaces: Close to N74C to N74D; towards the apex, close to 71A to 71B. Fully opened, upper and lower surfaces: Close to N74C to N74D; towards the apex, close to 71A to 71B; with development, color becoming closer to 75A to 75D with apex, close to 71B.

*Peduncles*.—Length: About 31.1 cm. Diameter: About 3.5 mm. Aspect: Mostly erect to 25° from vertical. Texture: Pubescent. Color: Close to 146A.

*Pedicels*.—Length: About 7.3 cm. Diameter: About 1.5 mm. Aspect: About 45° from the peduncle axis. Texture: Pubescent. Color: Close to 138A tinged with close to 201A to 201B.

*Reproductive organs*.—Androecium: Stamen number per flower: About 150. Filament length: About 4 mm. Filament color: Close to NN155C to NN155D. Anther shape: Reniform. Anther length: About 1 mm. Anther color: Close to 14A. Amount of pollen: Scarce. Pollen color: Close to 12B. Gynoecium: Pistil number per flower: About 200. Pistil length: About 1 mm. Stigma shape: Club-shaped. Stigma color: Close to 144B. Style length: About 0.5 mm. Style color: Close to 145A. Ovary color: Close to 145A. Seeds and fruits: Seed and fruit development have not been observed on plants of the new *Anemone*.

Garden performance: Plants of the new *Anemone* have been observed to have good garden performance, to tolerate high temperatures of about 35° C. and to be hardy to USDA Hardiness Zone 4.

Pathogen & pest resistance: Plants of the new *Anemone* have not been observed to be resistant to pests and pathogens common to *Anemone* plants.

It is claimed:

1. A new and distinct *Anemone* plant named 'Pretty Lady Julia' as illustrated and described.

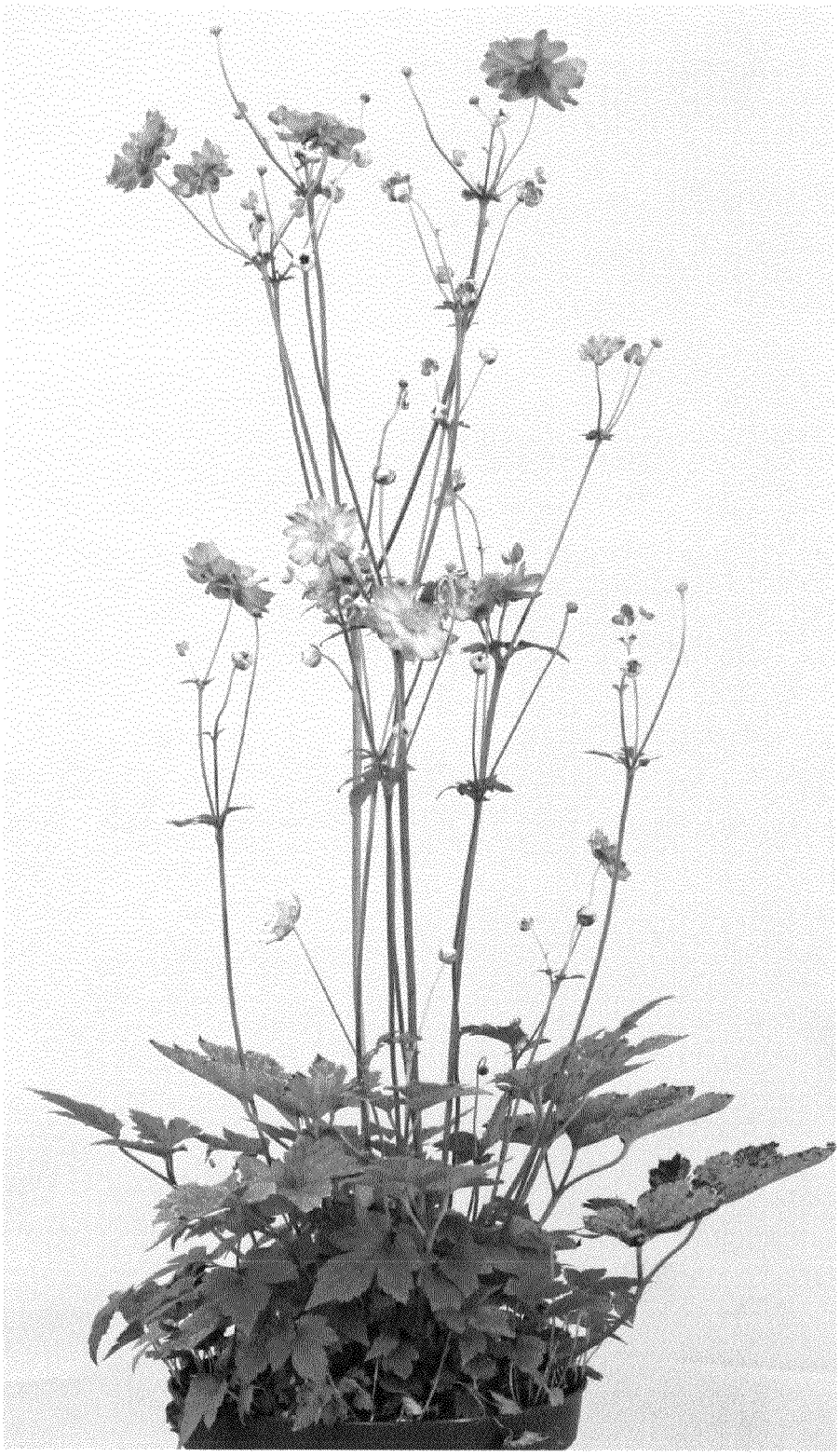

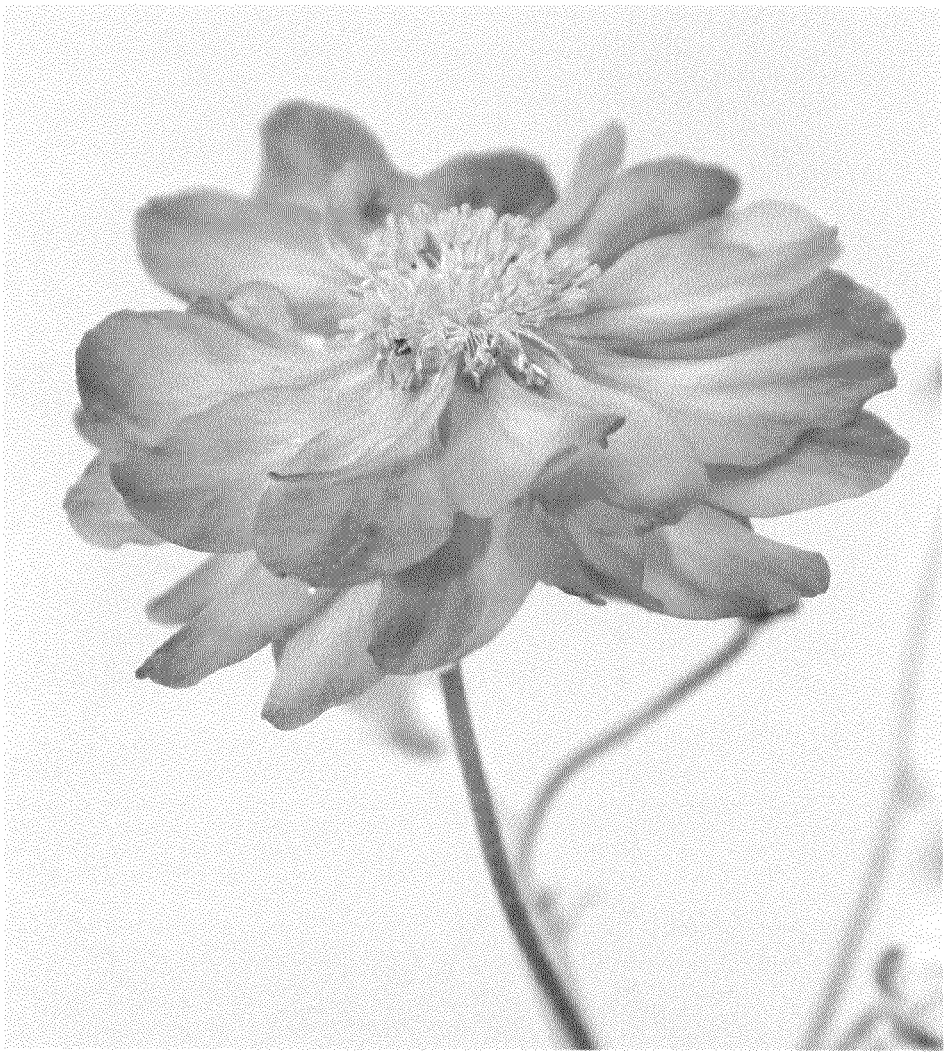

* * * * *